United States Patent
Tokuyasu et al.

(10) Patent No.: US 6,437,107 B1
(45) Date of Patent: *Aug. 20, 2002

(54) 2-METHYL-(4-O-(2-AMINO-2-DEOXY-β-GLUCOPYRANOSYL)-1,2-DIDEOXY-α-GLUCOPYRANO}(2,1-D)-2-OXAZOLINE AND ITS SALT, 50% DEACETYLATED CHITIN OR ITS OLIGOSACCHARIDE AND SALT THEREOF

(75) Inventors: Ken Tokuyasu, Tsukuba; Yutaka Mori, Ushiku; Yuki Kitagawa, Okazaki; Kiyoshi Hayashi, Tsuchiura, all of (JP)

(73) Assignee: Director of National Food Research Institute, Ministry of Agriculture, Forestry and Fisheries, Tsukuba (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/393,072

(22) Filed: Sep. 7, 1999

(51) Int. Cl.$^7$ .......................... C08B 37/08; C13K 13/00
(52) U.S. Cl. ..................... 536/20; 536/123.13
(58) Field of Search .................. 514/62, 55; 536/17.3, 536/18.7, 20, 123, 123.1, 123.13

(56) References Cited

U.S. PATENT DOCUMENTS

| | | | |
|---|---|---|---|
| 5,139,949 A | * 8/1992 | Matsuda et al. | 435/252 |
| 5,204,107 A | * 4/1993 | Tsurutani | 424/426 |
| 5,362,717 A | * 11/1994 | Dingilian et al. | 514/55 |
| 5,955,320 A | * 9/1999 | Tokuyasu | 435/84 |

FOREIGN PATENT DOCUMENTS

| | | |
|---|---|---|
| JP | 01079194 | * 3/1989 |
| JP | 03284690 | * 12/1991 |
| JP | 04074358 | * 11/1992 |
| JP | 09003088 | * 1/1997 |
| JP | 09132585 | * 5/1997 |

OTHER PUBLICATIONS

Kobayashi et al. Synthesis of Artificial Chitin: Irreversible Catalytic Behavior of a Glycosyl Hydrolase through a Transition State Analogue Substrate, JACS, vol. 118(51), pp. 13113–13114, Dec. 1996.*

Aiba et al. Preparation of higher N–acetylchitooligosaccharides in high yields. Kichin, Kitosan Kenkyu, vol. 4(2): 124–125, 1998.*

Kiyosada et al. Enzymic ring–opening polyaddition for chitin synthesis. A cationic mechanism in basic solution? Macromol. Symp., vol. 132 (Int. Symp. on Ionic Polymer.), pp. 415–420, 1998.*

Anthonsen et al. Solution properties of chitosans: conformation and chain stiffness with different degrees of acetylation. Carbohydrate Polymers, vol. 22, pp. 193–201, 1993.*

Hon et al. Chitins and Chitosans: Medical Applications (Chpt. 21) from Polysaccharides in Medicinal Applications, Edited by Severian Dumitriu, Publ. by Marcel Dekker, pp. 631–649, 1996.*

* cited by examiner

Primary Examiner—James O. Wilson
Assistant Examiner—Leigh C. Maier
(74) Attorney, Agent, or Firm—Frishauf, Holtz, Goodman & Chick, P.C.

(57) ABSTRACT

2-Methyl-{4-O-(2-amino-2-deoxy-β-glucopyranosyl)-1,2-dideoxy-α-glucopyrano}(2,1-d)-2-oxazoline of the following formula or an acid addition salt thereof

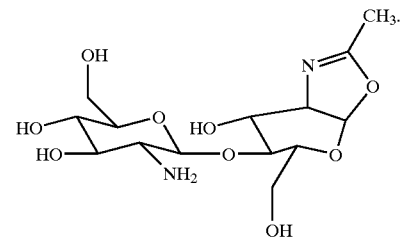

A 50% deacetylated chitin having a repeating structure represented by the following formula, an oligosaccharide thereof or an acid addition salt thereof

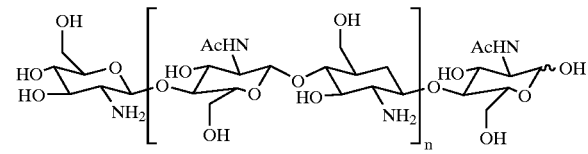

wherein n is an integer.

3 Claims, 4 Drawing Sheets

2-METHYL-{4-O-(2-AMINO-2-DEOXY-β-GLUCOPYRANOSYL)-1,2-DIDEOXY-α-GLUCOPYRANO}(2,1-D)-2-OXAZOLINE AND ITS SALT, 50% DEACETYLATED CHITIN OR ITS OLIGOSACCHARIDE AND SALT THEREOF

BACKGROUND OF THE INVENTION

1. Field of the Invention

The present invention relates to 2-methyl-{4-O-(2-amino-2-deoxy-β-glucopyranosyl)-1,2-dideoxy-α-glucopyrano}(2,1-d)-2-oxazoline, an acid addition salt thereof, 50% deacetylated chitin or an oligosaccharide thereof and acid addition salts thereof.

2. Background Information

Chitin, which is a biomass produced in abundance, is the straight-chain polymer of N-acetylglucosamine and obtained industrially by extracting from the outer shell of Crustacea.

However, there is no appropriate solvent for dissolving chitin, thereby making it difficult to prepare a derivative. Therefore, the application range of chitin as a raw material is narrow and its additional value is low. Since chitosan which is the deacetylated product of chitin dissolves in an acid, is very reactive and has an amino group which shows specific properties such as antifungal properties and cholesterol absorption suppression, it is easy to form derivatives from chitosan, chitosan is used in various fields, and both basic and applied research are now being carried out energetically.

Under the circumstances, it has been found that partly deacetylated chitin and a low molecular weight product thereof which are intermediates between chitin and chitosan show water solubility, high moisture retention and metal adsorption properties or high elicitor activity for plants and they are attracting much attention as a raw material having high applicability.

However, a process for producing partly deacetylated chitin is to deacetylate chitin in a concentrated alkali after it is highly swollen or to acetylate chitosan by adding a predetermined amount of acetic anhydride after it is dissolved, and hence has such a problem as the nonuniform distribution of acetyl groups and fluctuation in the quality of partly deacetylated chitin products.

When its elicitor activity for plants is subjected to an assay, it is extremely difficult to elucidate its action mechanism from the grasp of a phenomenon because a mixture of partly deacetylated chitin oligosaccharide obtained by hydrolyzing partly deacetylated chitin is used as an elicitor active substance and its structure is not uniform.

Further, substituents existent on formed partly deacetylated chitin and derivatives thereof such as oligosaccharide when a free amino group having high reactivity and residing on partly deacetylated chitin and an oligosaccharide etc. thereof is chemically modified are not aligned regularly, thereby causing differences in the quality of derivatives.

SUMMARY OF THE INVENTION

It is an object of the present invention to solve the above problems of the prior art and develop a further advanced application method for a chitin material.

The inventors of the present invention have conducted intensive studies to solve the above problems and have succeeded in the production of 2-methyl-{4-O-(2-amino-2-deoxy-β-glucopyranosyl)-1,2-dideoxy-α-glucopyrano}(2,1-d)-2-oxazoline which is a novel di-saccharide.

Further, they have found that 50% deacetylated chitin or an oligosaccharide thereof and salts thereof which are novel compounds can be synthesized by subjecting the compound to an enzyme catalyst addition polymerization reaction according to a known method. The present invention has been accomplished based on these facts.

The present invention concerns is 2-methyl-{4-O-(2-amino-2-deoxy-β-glucopyranosyl)-1,2-dideoxy-α-glucopyrano}(2,1-d)-2-oxazoline represented by the following formula (1) or an acid addition salt thereof.

Chemical Formula 1

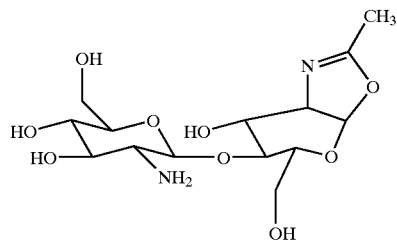

The present invention also relate to a is 50% deacetylated chitin having a repeating structure represented by the following formula (2) or an oligosaccharide thereof and acid addition salts thereof.

Chemical Formula 2

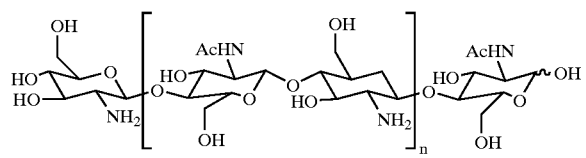

(wherein n is an integer)

Figure 1:
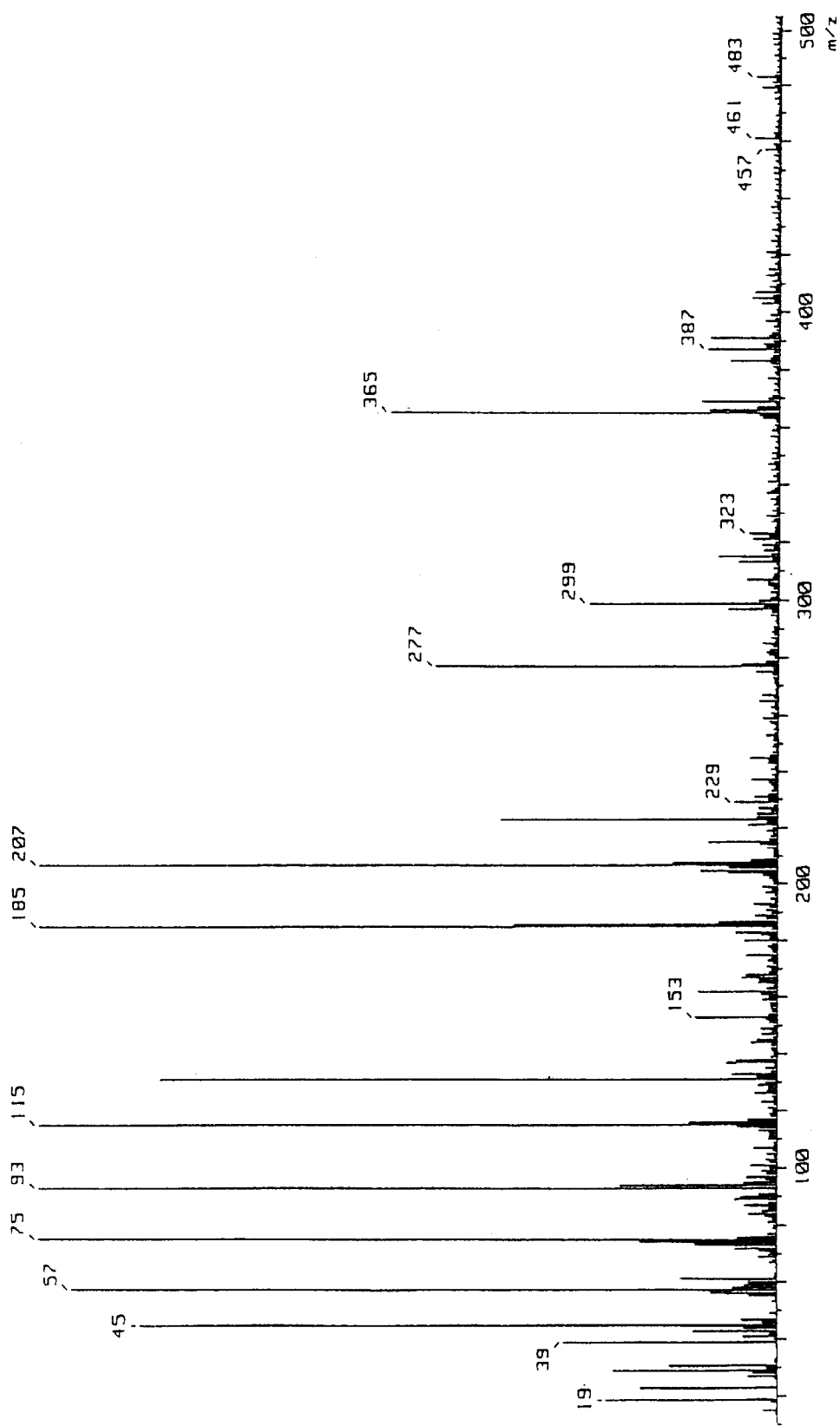
FIG. 1 shows the mass spectrum of the compound produced in Example 2.

DETAILED DESCRIPTION OF THE INVENTION 2-methyl-{4-O-(2-amino-2-deoxy-β-glucopyranosyl)-1,2-dideoxy-α-glucopyrano}(2,1-d)-2-oxazoline which is the novel substance of the present invention is obtained by deacetylating 2-methyl-{4-O-(2-acetamido-2-deoxy-β-glucopyranosyl)-1,2-dideoxy-α-glucopyrano}(2,1-d)-2-oxazoline which is a chitin dimer derivative having an oxazoline skeleton synthesized from a chitin dimer as a starting material. The chitin dimer derivative having this oxazoline skeleton can be produced by a known method. For example, it can be produced from di-N-acetylchitobiose hexaacetate as a starting material according to a reaction scheme A described in Japanese Patent Kokai No. Hei 9-3088.

The novel substance of the present invention can be obtained by deacetylating the above chitin dimer derivative having an oxazoline skeleton as a substrate. This deacetylation treatment is carried out enzymatically to eliminate only the acetyl group of sugar on a non-reduced terminal side of the substrate.

A deacetylation enzyme used for enzymatic deacetylation is, for example, a chitin deacetylating enzyme derived from an imperfect fungus, as exemplified by a chitin deacetylating enzyme derived from the *Colletotrichum lindemuthianum* ATCC 56676 strain (Biosci. Biotech. Biochem., 60 (10), 1598–1603, 1996) and the like. This enzyme can be obtained by a method described in Japanese Patent Kokai No. Hei 8-289785, for example.

That is, the enzyme can be obtained by culturing the spore of the above imperfect fungus in a liquid medium (composition: 0.28% of glucose, 0.123% of magnesium sulfate (heptahydrate), 0.2% of proteose peptone, 0.272% of potassium dihydrogen phosphate, 2.0% of agar) and collecting an active fraction from the cultured product. This can be used as a crude enzyme solution or purified in accordance with a commonly used method and used as a purified enzyme.

The novel substance of interest of the present invention can be produced by eliminating only the acetyl group of the residual N-acetylglucosamine group on the non-reduced terminal side of the substrate by making this enzyme act on the above substrate and converting it into the residual glucosamine group.

The enzymatic deacetylation will be described with reference to an example. A substrate prepared to a final concentration of 0.1 to 1.0%, preferably 0.8% and 0.5 to 20 units/ml, preferably 4 units/ml of said chitin deacetylating enzyme are mixed together, and the resulting mixture is treated in a 20 mM ammonium carbonate buffer solution (pH of 8.5) at 25 to 45° C., preferably 30° C. for 1 to 12 hours, preferably 2 to 4 hours.

Thus, 2-methyl-4-{4-O-(2-amino-2-deoxy-β-glucopyranosyl)-1,2- dideoxy-α-glucopyrano}(2,1-d)-2-oxazoline represented by said formula (1) is obtained. The acid addition salt includes a hydrochloride salt and acetate salt represented by the following formula.

Chemical Formula 3

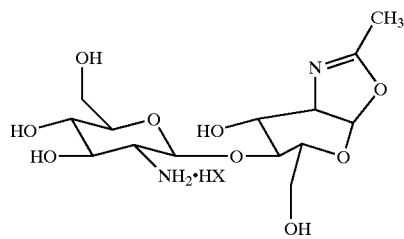

The 50% deacetylated chitin represented by said formula (2) or oligosaccharide thereof and acid addition salts thereof are compounds having such a structural feature that one out of two residual groups of sugar on the chitin chain is regularly deacetylated.

These compounds can be produced from the novel substance of the present invention represented by the formula (1) obtained as described above or from an acid addition salt thereof as a raw material to be synthesized.

That is, these compounds can be produced by subjecting the novel substance of the present invention represented by the formula (1) or an acid addition salt thereof to an enzyme catalyst addition polymerization reaction. The enzyme catalyst used herein includes chitinase derived from Bacillus etc.

The novel substance of the present invention represented by the formula (1) or an acid addition salt thereof is dissolved (appropriate final concentration is about 10 to 100 mM) in a buffer solution such as a sodium citrate buffer solution (pH of 6.0) and the enzyme is added to carry out an enzyme catalyst addition polymerization reaction at 25 to 45° C., preferably 40° C. so as to obtain an aimed compound represented by the formula (2). At this point, it is preferred to add 2-acetylamino-4-O-(2-amino-2-deoxy-β-D-glucopyranosyl)-2-deoxy-D-glucose to control the concentration to about 15 mM. The oligosaccharide and acid addition salts thereof can be obtained by freeze drying these compounds directly or after the addition of an acid or a volatile salt.

These compounds can be used as a plant elicitor or moisture retaining agent and novel compounds having the controlled conformational structure of amino groups or substituents can be synthesized by chemically modifying hydroxyl groups on the residual group of sugar or uniformly dispersed amino groups with an appropriate reagent using said compounds as starting materials.

There are known many methods for modifying a hydroxyl group or free amino group existent in the molecule of chitin or chitosan. For example, one skilled in the art can carry out a chemical modification reaction extremely easily in accordance with a manual such as "Chitin or Chitosan Experimental Manual" (edited by the Chitin and Chitosan Research Association and published by Gihodo Shuppan).

However, as the 50% deacetylated chitin having a repeating structure and represented by the above formula (2) or oligosaccharide thereof and acid addition salts thereof of the present invention are novel compounds which are intermediates between chitin and chitosan, the chemical modification of the compounds has a different meaning from the chemical modification of chitin or chitosan. Especially when free amino groups which are regularly aligned are to be chemically modified, a compound having substituents arranged regularly is formed, thereby making it possible to produce a derivative having more uniform properties than when existing partly deacetylated chitin is used as a substrate.

The compound of the present invention represented by said formula (1) and an acid addition salt thereof are units in the high polymerization through the enzyme catalyst addition polymerization reaction as described above and can be raw materials for the production of the compound of the present invention represented by the formula (2) or oligosaccharide thereof and acid addition salts thereof. Further, any deacetylated degree below 50% of chitin or oligosaccharide thereof and acid addition salts thereof can be synthesized by mixing with 2-methyl-{4-O-(2-acetamido-2-deoxy-β-glucopyranosyl)-1,2- dideoxy-α-glucopyrano}(2,1-d)-2-oxazoline (compound described in Japanese Patent Kokai No. Hei 9-3088) in a predetermined ratio to carry out an addition polymerization reaction in the same manner as described above.

EXAMPLES

The following examples are provided for the purpose of further illustrating the present invention but are in no way to be taken as limiting.

Example 1
(Purification of Chitin Deacetylating Enzyme)

The Colletotrichum lindemuthianum ATCC 56676 strain, an imperfect fungus, was inoculated into a medium containing 0.28% of glucose, 0.123% of magnesium sulfate (heptahydrate), 0.2% of proteose peptone, 0.272% of potassium dihydrogen phosphate and 2.0% of agar, left to stand and cultured in a dark place at 25° C. for 7 days to derive a black cell.

Thereafter, said cell was inoculated into a 500 ml conical flask filled with 200 ml of a medium (pH of 5.8) containing 1% of a malt extract, 0.4% of a yeast extract and 0.4% of glucose and cultured by shaking at 100 rpm in a dark place at 22° C. During culture, the enzymatic activity of the culture solution was measured by an indole hydrochloride method (J. Biol. Chem., 184, 517-522 (1950)). As a result, from about 8-th day, what showed enzymatic activity began to be secreted in the culture solution and said activity increased until the 18-th day.

The culture was terminated on the 18-th day from the start of culture, and then after the cell culture solution was filtered with a nylon filter, fine particles were removed by passing through a glass fiber and a culture filtrate was collected.

Ammonium sulfate was added to the thus obtained culture filtrate to a saturation of 80% at 4° C. and left to stand over one night, and a precipitate was collected by centrifugation. This precipitate was dissolved in a small amount of 50 mM sodium tetraborate-hydrochloric acid buffer solution (pH of 8.5) and dialyzed in the same buffer solution.

The crude enzyme solution after dialysis was placed on the Butyl Toyopearl Column (of Toso Co., Ltd.) to elute the enzyme with the straight gradient of the concentration of ammonium sulfate and collect it which was then dialyzed with the same 1 mM buffer solution. After dialysis, a 200 mM triethanolamine-hydrochloric acid (TEA-HCl) buffer solution (pH of 7.5) was added to the collected enzyme solution to adjust the final concentration of the buffer solution to 20 mM, and the resulting buffer solution was placed on the O-Sepharose FAST FLOW (of Falmacia Co., Ltd.). The enzyme was eluted with the straight gradient of the concentration of sodium chloride and an active fraction was dialyzed with a 20 mM TEA-HCl buffer solution (pH of 7.5) to obtain a crude enzyme solution.

Thereafter, this crude enzyme solution was placed on the Resource O Column (of Falmacia Co., Ltd.) and the enzyme was eluted with the straight gradient of the concentration of sodium chloride to collect an active fraction and store it at 4° C. As a result, the enzyme was purified at a collection rate of 4.05% and a purification degree of 944 folds and showed a single band on an SDS-PAGE gel (molecular weight of about 31,500, molecular weight by gel filtration method of about 33,000).

When the characteristic properties of the obtained purified enzyme were measured, they were the same as described in Example 3 of Japanese Patent Kokai No. Hei 8-289785.

Production Example 1

2-methyl-{4-O-(2-acetamide-2-deoxy-β-glucopyranosyl)-1,2- dideoxy-α-glucopyrano}(2,1-d)-2-oxazoline was produced in accordance with the method described in Example 1 of Japanese Patent Kokai No. Hei 9-3088. That is, di-N-acetylchitobiose hexaacetate was dissolved in methanol and sodium methoxide was added to carry out a reaction so as to obtain a partly acetylated di-N-acetylchitobiose mixture.

Thereafter, acetyl chloride was added to said mixture to carry out a reaction so as to obtain 3,6-di-O-acetyl-2-acetamido-2-deoxy-4-O-[3,4,6-tri-O-acetyl-2-acetamido-2-deoxy-β-glucopyranosyl]-glucopyranosyl chloride.

The above compound was dissolved in acetonitrile and tetraethyl ammonium chloride and sodium hydrogen carbonate were added to carry out a reaction so as to obtain 2-methyl-{3,6- di-O-acetyl-4-O-[3,4,6-tri-O-acetyl-2-acetamido-2-deoxy-β-glucopyranosyl]-1,2-dideoxy-α-glucopyrano}[2,1-d]-2-oxazoline which was then dissolved in chloroform, and anhydrous methanol was added to this solution. Further, sodium methoxide was added to carry out a reaction to obtain the above compound.

Example 2

2-methyl-{4-O-[2-acetamido-2-deoxy-β-glucopyranosyl]-1,2-dideoxy-α-glucopyrano}(2,1-d)-2-oxazoline obtained in Production Example 1 was mixed with the purified chitin deacetylating enzyme (4 units/ml) obtained in Example 1 to a final concentration of 0.8% and an enzymatic deacetylation reaction was carried out in a 20 mM ammonium carbonate buffer solution (pH of 8.5) at 30° C.

The change of the substrate by the enzymatic reaction was observed by high-speed liquid chromatography (to be abbreviated as HPLC hereinafter). The conditions of HPLC are as follows.

conditions of HPLC column: Asahipak $NH_2$-P50 (of Shimadzu Corporation)

elute: water/acetonitrile=25/75 flow rate: 1 ml/min detector: UV-8020 (of Toso Co., Ltd.)

detection wavelength: UV 210 nm

As a result, a peak derived from a compound different from a chitin dimer having an oxazoline skeleton as a reaction substrate, a chitin dimer obtained by opening a ring thereof and a compound obtained by deacetylating the residual N-acetyl glucosamine group at the non-reduced terminal of a chitin diner grew along with a reduction in the amount of the substrate.

When this peak fraction was collected and analyzed by a mass spectrometer (of JEOL Co., Ltd.) after concentration, a signal with $[M+H^+]=365$ was detected and the fraction was estimated to have a molecular weight of 364. The mass spectrum of the fraction is shown in FIG. 1.

Figure 2:
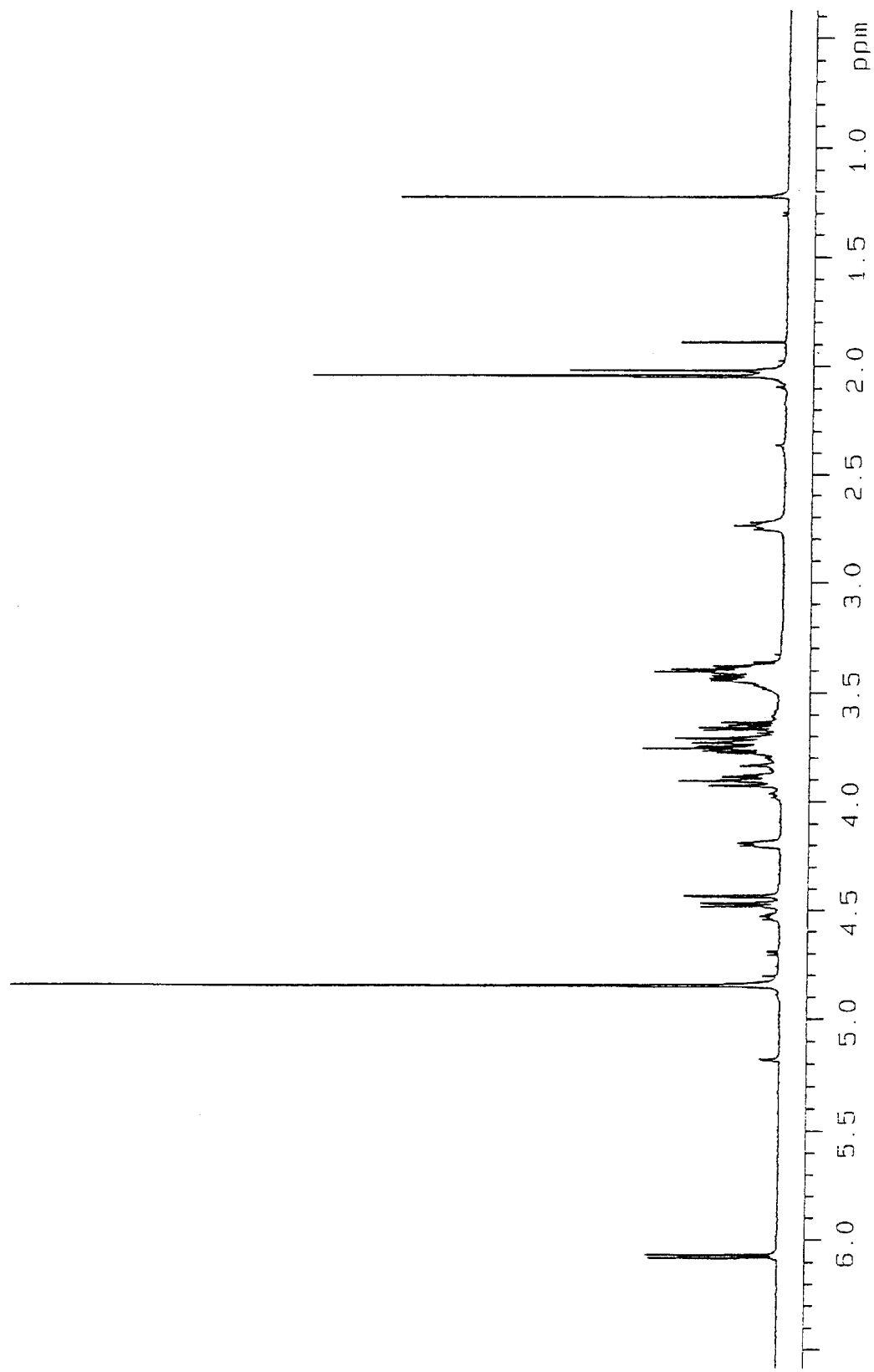
FIG. 2 shows the $^1$H-NMR spectrum of the compound produced in Example 3.

When it was further analyzed by $^1$H-NMR, it was confirmed that the compound was a novel substance, 2-methyl-{4-O-(2-amino-2-deoxy-β-glucopyranosyl)-1,2-dideoxy-α-glucopyrano}(2,1-d)-2-oxazoline. The $^1$H-NMR spectrum of the compound is shown in FIG. 2.

Example 3

The 100 mM of 2-methyl-{4-Q-(2-amino-2-deoxy-β-glucopyranosyl)-1,2- dideoxy-α-glucopyrano}(2,1-d)-2-oxazoline produced in Example 2 was dissolved in 0.1 ml of a 10 mM sodium citrate buffer solution (pH of 6.0) (final concentration of 0.2%), 2-acetylamino-4-O-(2-amino-2-deoxy-β-D-glucopyranosyl)-2-deoxy-D-glucose was added (final concentration of 15 mM), and 80 μg of chitinase derived from Bacillus (of Seikagaku Kogyo Co., Ltd.) was further added to carry out an enzyme catalyst addition polymerization reaction at 40° C. which was observed by HPLC. The conditions of HPLC are as follows.

conditions of HPLC column: Asahipak $NH_2$-P50 (of Shimadzu Corporation)

elute: water/acetonitrile=25/75 flow rate: 1 ml/min detector: UV-8020 (of Toso Co., Ltd.)

detection wavelength: UV 210 nm

Figure 3:
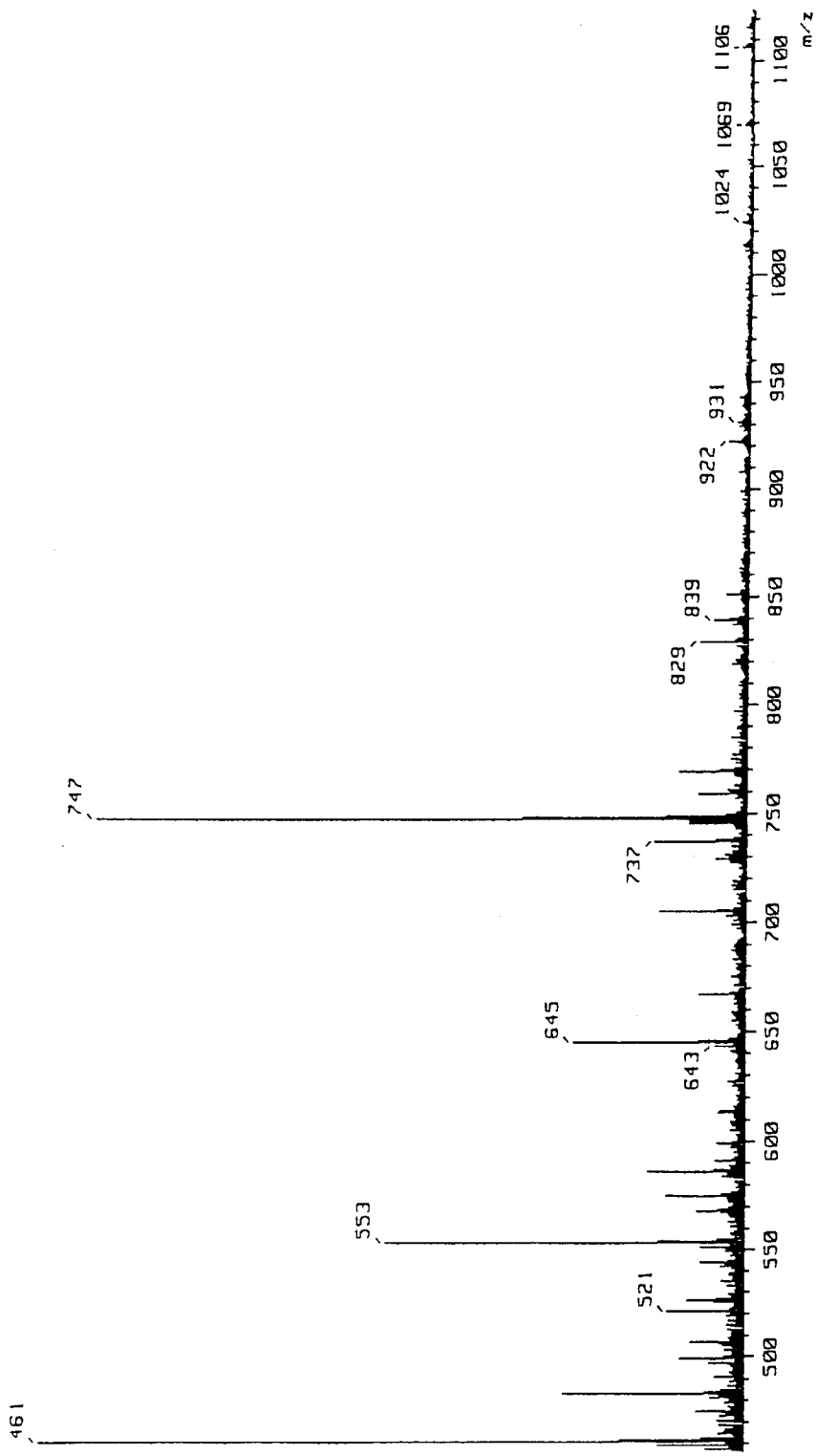
FIG. 3 shows the mass spectrum of the compound produced in Example 3.

As a new peak was detected at a retention time of 15 minutes, this peak fraction was collected and analyzed by a mass spectrometer (of JEOL Co., Ltd.) after concentration. As a result, a signal with [M+H+]=747 was detected and the fraction was estimated to have a molecular weight of 746. The mass spectrum of the fraction is shown in FIG. 3.

Figure 4:
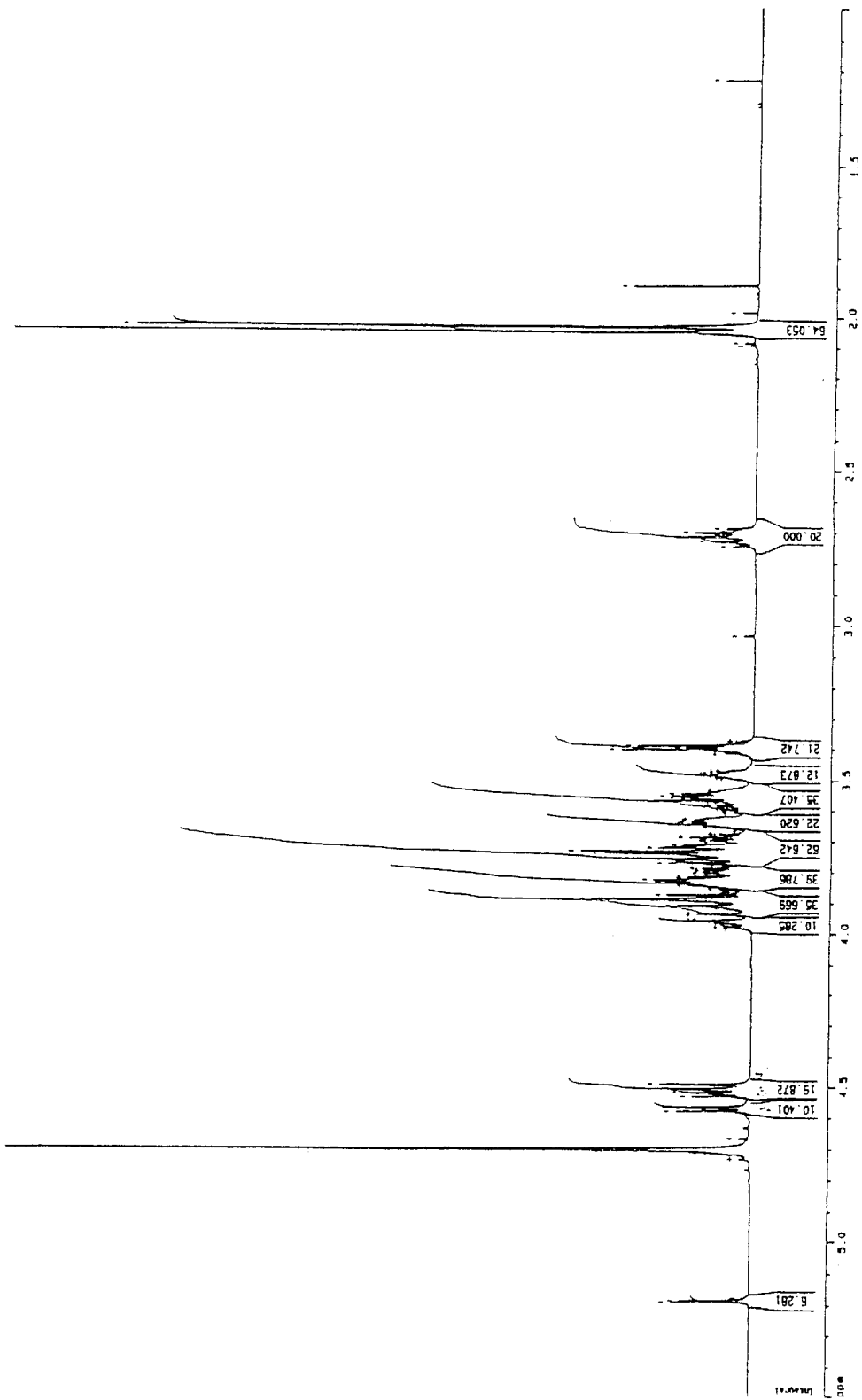
FIG. 4 shows the $^1$H-NMR spectrum of the compound produced in Example 3.

When it was further analyzed by $^1$H-NMR etc., it was confirmed that said compound was a compound obtained by eliminating the acetyl groups of the residual first and third N-acetyl glucosamine groups from the non-reduced terminal side of a chitin tetramer. The $^1$H-NMR spectrum of the compound is shown in FIG. 4.

COMMERICAL APPLICABILITY OF THE INVENTION

According to the present invention, there are provided partly acetylated 2-methyl-{4-O-(2-amino-2-deoxy-β-glucopyranosyl)-1,2- dideoxy-α-glucopyrano}(2,1-d)-2-oxazoline which is an intermediate between chitin and chitosan, an acid addition salt thereof, 50% deacetylated chitin or oligosaccharide thereof and acid addition salts thereof.

Since 50% deacetylated chitin which is deacetylated regularly or an oligosaccharide etc. thereof can be prepared, chitin-related materials maintaining fixed quality can be provided and can pave the way to the advanced application of chitin materials, which are a waste resource, in the medical field and the like.

What is claimed is:

1. 2-Methyl-{4-O-(2-amino-2-deoxy-β-glucopyranosyl)-1,2-dideoxy-α-glucopyrano}(2,1-d)-2-oxazoline represented by the following formula (1) or an acid addition salt thereof

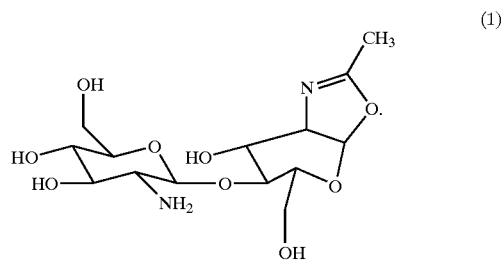

(1)

2. An acid addition salt of the compound of formula (1) of claim 1, wherein the salt is a hydrochloride salt.

3. An acid addition salt of the compound of formula (1) of claim 1, wherein the salt is an acetate salt.

* * * * *